United States Patent
Minott et al.

(10) Patent No.: US 7,574,899 B2
(45) Date of Patent: Aug. 18, 2009

(54) FLUID CONTAMINANT DETECTION DEVICE

(75) Inventors: Bruce Ross Minott, Anaheim, CA (US);
Tak-Yiu Wong, Cerritos, CA (US);
Timothy Allen Dalton, Fountain Valley, CA (US)

(73) Assignee: Argo-Tech Corporation Costa Mesa, Costa Mesa, CA (US)

(*) Notice: Subject to any disclaimer, the term of this patent is extended or adjusted under 35 U.S.C. 154(b) by 2 days.

(21) Appl. No.: 11/625,689

(22) Filed: Jan. 22, 2007

(65) Prior Publication Data

US 2008/0174442 A1    Jul. 24, 2008

(51) Int. Cl.
*G01N 33/22* (2006.01)
*G01N 33/26* (2006.01)
*G01R 27/26* (2006.01)

(52) U.S. Cl. ............... 73/61.43; 73/61.41; 324/689
(58) Field of Classification Search ............... 73/61.41, 73/61.43, 61.44; 340/627; 324/689
See application file for complete search history.

(56) References Cited

U.S. PATENT DOCUMENTS

| 4,316,174 | A | * | 2/1982 | Sutton et al. ............... 340/438 |
| 4,349,882 | A | * | 9/1982 | Asmundsson et al. ......... 702/52 |
| 5,033,289 | A | * | 7/1991 | Cox ........................... 73/61.43 |
| 6,885,199 | B2 | * | 4/2005 | Desmier et al. ............. 324/663 |

* cited by examiner

*Primary Examiner*—Daniel S Larkin
(74) *Attorney, Agent, or Firm*—Kelly Lowry & Kelley LLP

(57) ABSTRACT

A contaminant detector disposed within a base fluid for detecting the presence of a contaminating fluid includes a conductive core, a conductive sensor probe extending from the core in non-conductive relation, and a circuit board within the core. The circuit board is electrically connected to the sensor probe and electrically insulated from the core. Electrical power applied to the core creates a closed field loop for measuring the localized capacitance of the base fluid. When sufficient contaminating fluid exists in the base fluid to change the localized capacitance, an alarm is sounded to indicate the presence of the contaminating fluid.

26 Claims, 4 Drawing Sheets

FLUID CONTAMINANT DETECTION DEVICE

BACKGROUND OF THE INVENTION

For almost all combustion engine vehicles such as automobiles, aircraft and boats, small amounts of water contained in the liquid fuel will downgrade the performance of the combustion engine. Excessive amounts of water in the liquid fuel could cause a failure of combustion and result in a catastrophic failure at the cost of equipment and/or human life.

Water can be easily introduced into liquid fuel tanks through either natural means, such as condensation, or through human error. The fuel system industry has paid special attention to preventing water from entering vehicle fuel tanks and fueling systems. Many fueling systems are designed to incorporate filters/treaters/processors that remove water and/or particles during the tank filling process. Water can accumulate in the storage tanks from condensation and ambient temperature changes. Additional onboard filtering systems are needed to insure that all the water has been removed from the fuel prior to the fuel being sent to the engine to be burned. While it is the function of the fuel filtration system to effectively remove water, it is also known that these filtration elements can degrade from excessive water and/or other contaminants in the fuel itself.

A number of existing water detection devices are currently used in the fuel system filtration industry. Many of these existing designs take advantage of the higher density of water compared to the most common petroleum base liquid fuel. Other designs use the electrical conductivity of water to complete an electrical circuit to indicate the presence of water. As water is filtered out of the fuel, it accumulates at the lowest point in the fueling tank, normally in the bottom of the filter vessel. It is at this location that the water detection device is installed. Prior detection devices can normally be categorized as either a mechanical or electrical devices.

The most common type of mechanical detection device includes a buoy. The buoy is weighted such that it will not float in pure fuel. Therefore, the buoy will stay in the down position when the tank is filled with pure fuel. When sufficient contaminant water has accumulated, the buoy floats and triggers an alarm and/or shutdown. A disadvantage of the mechanical design is that it has a number of moving parts that can easily become jammed by contaminants commonly found in the water that accumulates in the harsh environment at the bottom of a fuel tank or filter vessel.

The most common type of electrical water detector utilizes the electrical conductivity of water versus the non-conductive fuel as the means to detect the existence of accumulated water. This is an effective means to detect water in a relatively clean environment. However, petroleum fuel when mixed with water provides a hospitable environment for bacterial micro-growth. This bacteria can form an electrically insulated film over the water detector isolating the sensing electrodes from the water rendering the detector useless.

Another drawback with the existing water detector designs is that the fueling industry normally demands that the detector be periodically certification tested to insure its proper function. For most prior art water detectors, water is introduced into the fuel system in order to perform a realistic function test. This practice contradicts the requirement to remove water from the fuel system. The industry is reluctant to perform this action but quite often forced to accept it due to the lack of a better choice.

Accordingly, there is a need for a contaminant detection device with few moving parts that can become jammed by contaminants, and that is not susceptible to failure from bacterial growth on the sensing electrodes. Moreover, a contaminant detection device is needed which eliminates the undesirable practice of having to introduce water into the fueling system for a realistic function test. Such a new contaminant detection device must provide an effective means of alerting the fueling system operator when excessive amounts of contaminant are accumulated in the fuel/water separator vessel. With an additional control subsystem, this detection device can also disable the fueling system to prevent the malfunctioning filter element from passing water downstream. The present invention fulfills these needs and provides other related advantages.

SUMMARY OF THE INVENTION

The present invention is directed to a contaminant detector disposed within a base fluid for detecting the presence of a contaminating fluid. The contaminant detector comprises a conductive housing, a conductive core slidingly disposed within the housing, a conductive sensor probe extending from the core in non-conductive relation, means for charging the sensor probe and providing an opposite electrical charge to the core and housing to create a closed field loop through the base fluid, means for measuring the localized capacitance of the base fluid in proximity to the sensor probe in the housing, and means for producing an alarm signal in response to a change in the measured localized capacitance to indicate the presence of the contaminating fluid in the base fluid above a pre-set threshold.

The housing extends from the proximate end of the core to beyond the distal end of the core and is configured such that the sensor probe extends beyond the distal end of the housing in non-conductive relation. A sliding seal between the proximate end of the core and the housing prevents fluid from leaking through.

A sensor cap is mounted over that portion of the sensor probe that extends beyond the housing and a spring biases the sensor probe away from the housing. The spring in conjunction with the sensor cap maintains the sensor probe a fixed distance from the housing. An insulating washer between the sensor cap and the housing maintains the sensor probe in electrical isolation from the housing. Two or more openings in the housing adjacent to the sensor probe permit the passage of fluid into the housing to reach the sensor probe.

An insulator seal cartridge between the core and the sensor probe maintains the electrical isolation therebetween. In addition, an insulator also maintains the electrical isolation of the sensor probe from the core. In a preferred embodiment the base fluid comprises a fuel and the contaminating fluid comprises water.

The contaminant detector may be used in a process for detecting the presence of a contaminating fluid in a base fluid comprising the steps of:

Positioning a contaminant detector having a conductive core, a sensor probe extending from the core in non-conductive relation and a circuit board electrically coupled to the sensor probe, in a tank containing the base fluid;

Applying electrical power to the circuit board;

Creating an electrical charge in the sensor probe and an opposite electrical charge in the core to create a closed field loop through the base fluid;

Measuring the localized capacitance of the base fluid in proximity to the sensor probe and the core; and Producing an alarm signal in response to a change in the measured localized capacitance to indicate the presence of the contaminating fluid in the base fluid above a preset threshold.

The contaminant detector may also include a conductive housing in which the core is slidingly disposed and the sensor probe is disposed in non-conductive relation. With the housing, the creating step includes the step of creating the opposite electrical charge in the housing and the measuring step includes the step of measuring the capacitance of the base fluid through the housing.

A contaminant detector may be mounted vertically in a bottom wall of the tank or horizontally in a side wall of the tank. In a preferred embodiment the base fluid comprises a fuel and the contaminating fluid comprises water. The circuit board is preferably enclosed within the core and electrical power is provided from a source external to the tank.

Testing of the contaminant detector can be achieved by biasing the sensor probe a set distance away from the housing. The sensor probe is then pushed to within a predetermined distance of the housing against the biasing. An alarm signal is produced in response to the measured localized capacitance. The pushing of the sensor probe changes the localized capacitance between the sensor probe and the housing such that it approaches the localized capacitance when the sensor probe is biased a set distance away from the housing and an amount of the contaminating fluid in the base fluid is above the preset threshold.

Other features and advantages of the present invention will become apparent from the following more detailed description, taken in connection with the accompanying drawings, which illustrate, by way of example, the principles of the present invention.

BRIEF DESCRIPTION OF THE DRAWINGS

The accompanying drawings illustrate the invention. In such drawings.

DETAILED DESCRIPTION OF THE PREFERRED EMBODIMENTS

The present invention is directed to a contaminant detector 10 for detecting the presence of a contaminating fluid in a base fluid. The following detailed description will describe the detector 10 in terms of a fueling system water detection device that detects the presence of water accumulated in the bottom of a fuel tank. However, the principles of the invention are applicable to systems for the detection of contaminants other than water in the presence of base fluids other than fuel.

Figure 1:
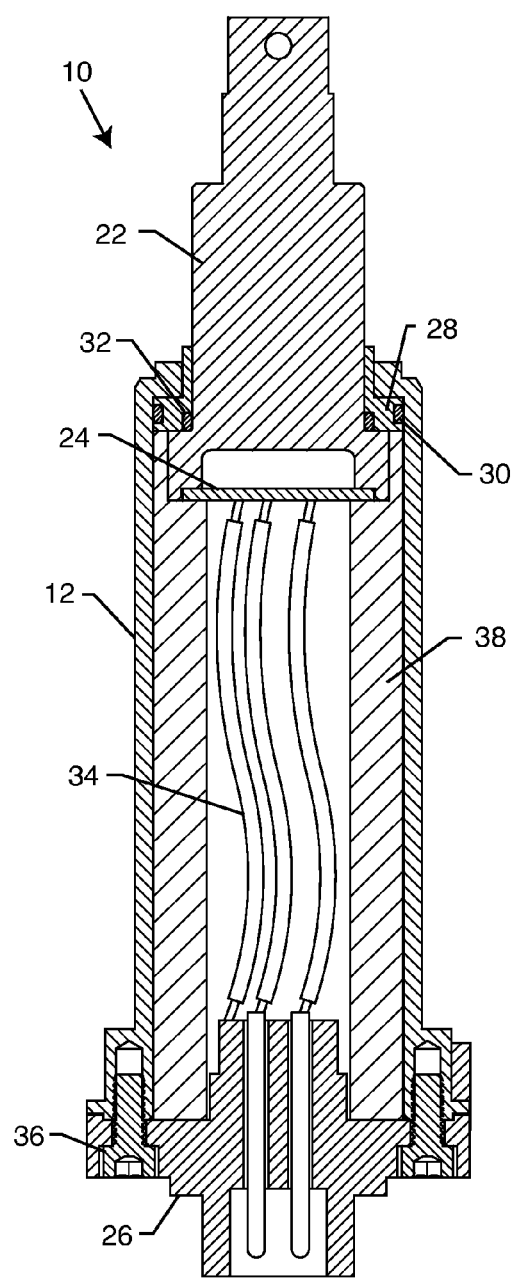
FIG. 1 is a cross-sectional view of the conductive core of a contaminant detector embodying the invention.
Figure 2:
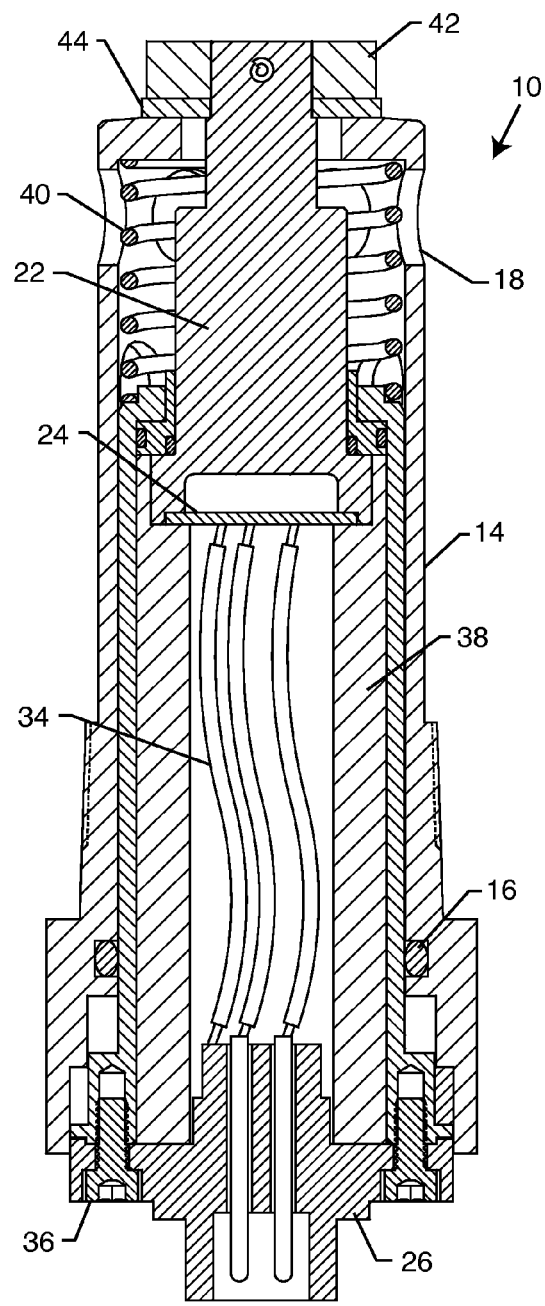
FIG. 2 is a cross-sectional view similar to FIG. 1, illustrating the conductive core slidably disposed in a housing.

As shown in FIGS. 1 and 2, the contaminant detector 10 consists primarily of a conductive core 12 in a conductive housing 14. The detector 10 includes a sliding seal 16 adjacent a proximate end of the detector 10 and the housing 14 includes one or more openings 18 adjacent the distal end of the detector 10.

The conductive core 12 has a sensor probe 22 that extends from the core 12 in non-conductive relation, and a circuit board 24 electrically coupled to the sensor probe 22. The core 12 is configured such that it fits snugly inside the housing 14 of the detector 10. The sensor probe 22 is positioned at the distal end of the core 12 such that at least a portion of the sensor probe 22 is external to the core 12. An insulator seal cartridge 28 is positioned around the junction between the core 12 and the sensor probe 22. Seals 30 and 32 create a fluid seal which prevents the passage of any fluid to the inside of the core 12.

The circuit board 24 is positioned inside the core 12 and electrically connected to the sensor probe 22. The circuit board 24 is also electrically connected to a connector assembly 26 by wires 34 or other means commonly known in the art. The connector assembly 26 is positioned at the proximate end of the core 12 and retained in place by fasteners 36. An insulator 38 is positioned inside the core 12 to electrically insulate the sensor probe 22 and circuit board 24 from the core 12. The insulator seal cartridge 28 also assists in this electrical insulation. The insulator 38 and insulator seal cartridge 28 are made from dielectric material.

The core 12 and housing 14 are both conductive. However, the present invention does not require electrical current to pass through the core 12, the housing 14 or the base fluid. The core 12 and the housing 14 possess a relatively low capacitance with each other, which assists in generating a closed field loop as described below A spring 40 is positioned inside the housing 14 between the distal end of the housing and the distal end of the core 12. At least a portion of the sensor probe 22 extends beyond the distal end of the housing 14. A sensor cap 42 is affixed to that portion of the sensor probe 22 that extends beyond the distal end of the housing 14. An insulator washer 44 is positioned between the sensor cap 42 and the housing 14 to maintain the electrical insulation of the sensor probe from the housing 14 and core 12. The spring 40 in combination with the sensor cap 42 biases the sensor probe 22 a fixed distance away from the housing 14. As will be described below this fixed distance biasing is necessary for the operation of the contaminant detector 10.

Figure 3:
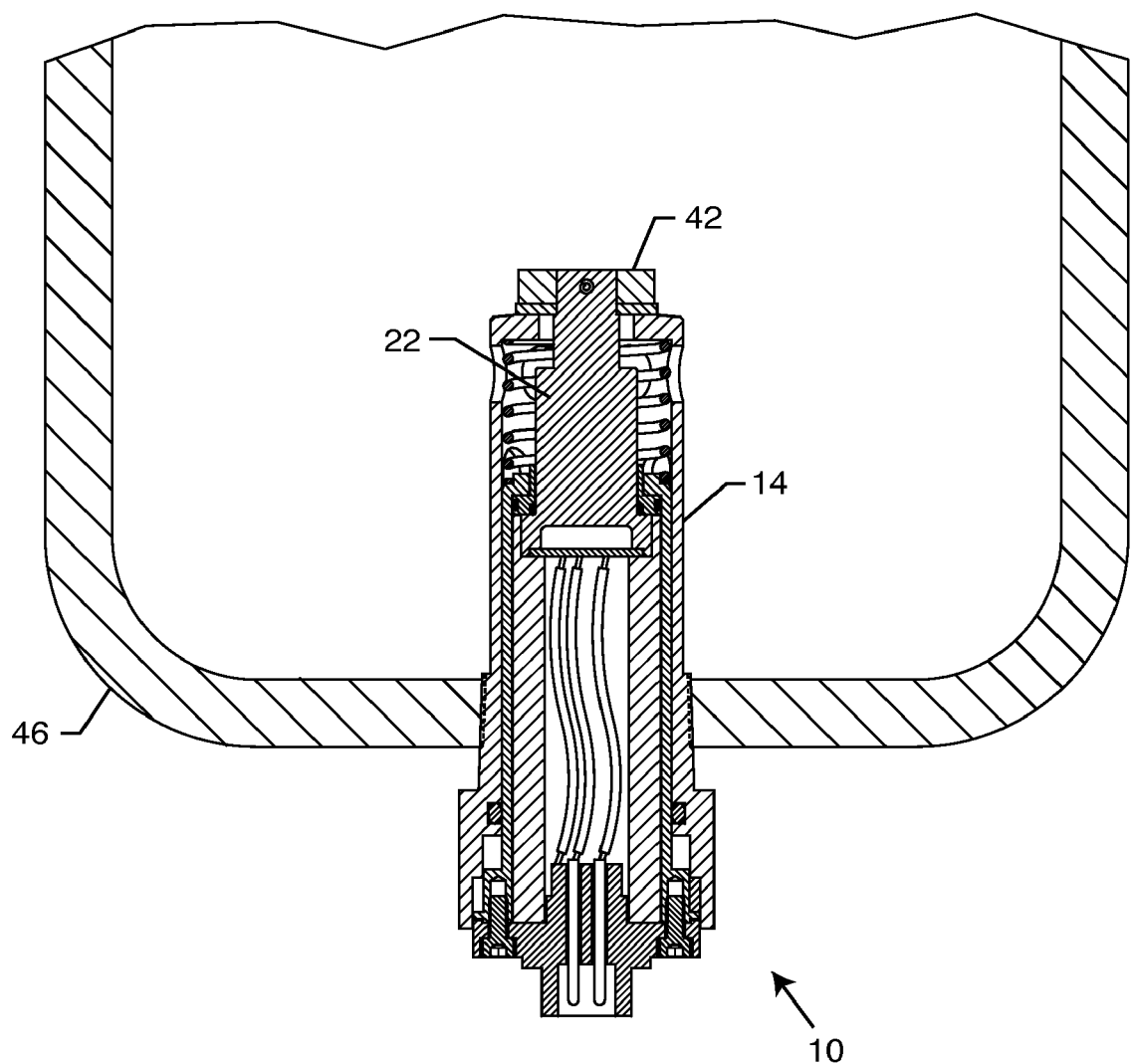
FIG. 3 is a fragmented cross-sectional view of the contaminant detector of FIG. 2 mounted in the bottom of a fuel tank.
Figure 4:
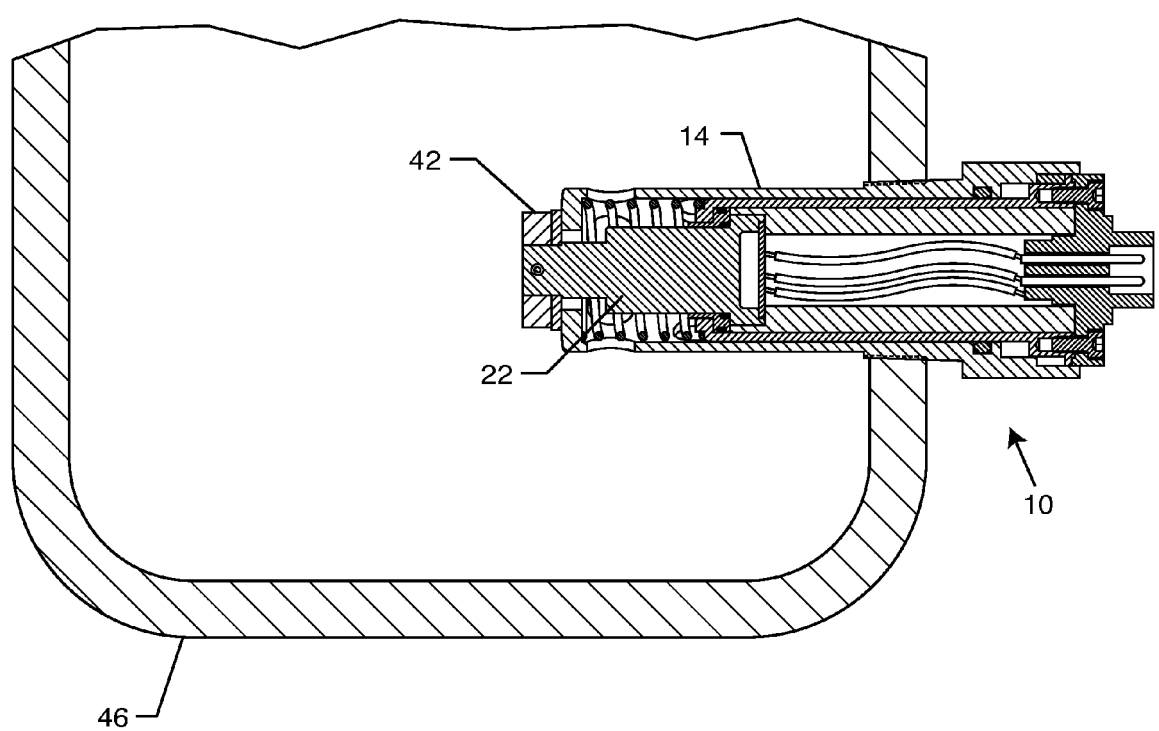
FIG. 4 is a fragmented cross-sectional view similar to FIG. 3, illustrating the contaminant detector mounted in a sidewall of the fuel tank.

As shown in FIGS. 3 and 4, the contaminant detector 10 may be mounted in the bottom wall or sidewall of a fuel tank 46. When the detection device assembly 10 is mounted in a fuel tank 46 the openings 18 in the distal end of the housing 14 allow liquid fuel or liquid water to reach the sensor probe 22. The seals 30 and 32 in the insulator seal cartridge 28 prevent fuel or water from entering the inside of the core 12 and interfering with the electronic parts therein. The sliding seal 16 in the housing prevents any external leakage between the housing 14 and the core 12.

In operation, electrical power is supplied to the circuit board 24 through the connector assembly 26. The electronic circuit board 24 creates an electrical charge to the sensor probe 22 and an opposite electrical charge to the core 12 and housing 14. The sensor probe 22 on the one hand and the core 12 and housing 14 on the other hand serve the function of sensing electrodes. These sensing electrodes with opposite charges actively project a "closed field loop" through the liquid fuel in their proximity. Using the "closed field loop", the circuit board 24 measures the capacitance through the liquid in the proximity of the sensing electrodes. In the presence of pure fuel, the capacitance measured by the circuit board 24 is a known value. When water accumulates in the fuel tank and the water level reaches a close proximity to both the sensor probe 22 and the core 12/housing 14, the circuit board 24 measures changes in the localized capacitance. When the capacitance changes by a predetermined magnitude, indicating the presence of too much water, the circuit board 24 produces an output alarm signal through the connector assembly 26 to an external alarm system (not shown).

It is not necessary that the contaminant water actually contact the sensor probe 22 or core 12/housing 14. Because the capacitance is measured using the closed field loop, the alarm output signal can be generated as the water level merely approaches the sensor probe 22 or core 12/housing 14. It is this feature that allows the circuit board 24 to detect the presence of water even if the sensing electrodes are covered with a film of bacterial micro growth, contaminants, corrosion, etc. The water detection function of the present invention is performed solely through electronic means without any mechanical moving parts.

Figure 5:
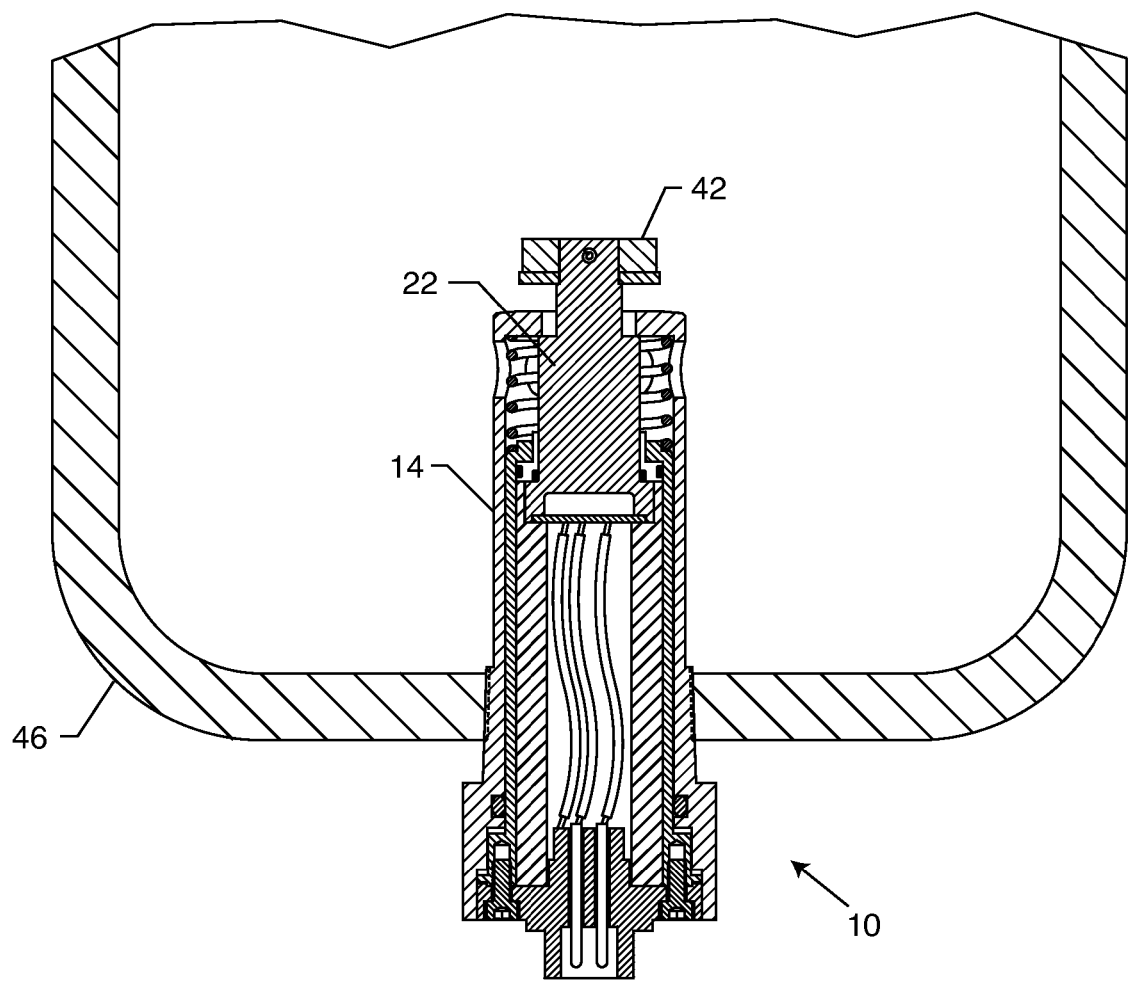
FIG. 5 is a fragmented cross-sectional view similar to FIG. 3, showing the contaminant detector mounted in the bottom wall of a fuel tank while in a testing mode.

In a testing mode of the present invention, the contaminant detector 10 is designed to incorporate a test feature which simulates the presence of water in proximity to the sensing electrodes without the actual introduction of water. As described in the operation mode, the circuit board 24 measures any variation of the localized capacitance in order to determine the presence of water in proximity to the sensing electrodes. The variation of localized capacitance can be simulated by varying the distance between the sensor probe 22 and the housing 14. As illustrated in FIG. 5, the core 12 can be pushed toward the housing 14 against the biasing of the spring 40. As the sensor probe 22 approaches the housing 14 to within a predetermined distance, the localized capacitance between the sensor probe 22 and housing 14 approach the capacitance measured in the operation mode of the detector 10 in the presence of water. In this testing mode, an output signal will be sent to the external alarm system by the circuit board 24, simulating the detection of excessive accumulated water in the fuel tank 46. Therefore, testing of the detection device assembly can be achieved without the introduction of water into the fuel tank 46.

The function of the housing 14 in the present invention is to facilitate testing of the contaminant detector 10 without the introduction of water into the fuel tank 46. In situations where the testing requirements are not applicable, the core 12 can be used independently as the contaminant detector 10 without the inclusion of the housing 14. In this case, the sensor core 12 may be mounted directly into the fuel tank 46.

As mentioned above, the contaminant detector 10 of the present invention may be applied to the detection of the presence of any undesirable fluid in another. For the technology to be applicable, the subject fluids must possess the following physical and electrical properties:

The fluids must not be soluble in one another;
The fluids must be of different densities such that they will separate from one another in gravity; and
The fluids must have different dielectric properties.

The placement of the contaminant detector 10 in the tank 46 may have to be changed depending upon the relative densities of the subject fluids. If the base fluid is more dense than the contaminant fluid then the contaminant fluid will float on top of the base fluid. In this case the contaminant detector 10 will need to be positioned such that it is near the area of the tank 46 in which the contaminant fluid will settle.

Although various embodiments of the present invention have been described in detail for purposes of illustration, various modifications may be made without departing from the scope and spirit of the invention.

What is claimed is:

1. A process for detecting the presence of a contaminating fluid in a base fluid, comprising the steps of:
   positioning a contaminant detector having a conductive core, a sensor probe extending from the core in non-conductive relation, and a circuit board electrically coupled to the sensor probe, in a tank containing the base fluid;
   applying electrical power to the circuit board;
   creating an electrical charge in the sensor probe and an opposite electrical charge in the core to create a closed field loop through the base fluid;
   measuring localized capacitance of the base fluid in proximity to the sensor probe and the core; and
   producing an alarm signal in response to a change in the measured localized capacitance to indicate the presence of the contaminating fluid in the base fluid above a pre-set threshold.

2. The process of claim 1, including a conductive housing in which the core is slidingly disposed in conductive relation.

3. The process of claim 2, wherein the creating step includes the step of creating the opposite electrical charge in the housing.

4. The process of claim 2, further comprising the steps of:
   biasing the sensor probe a set distance away from the housing;
   pushing the sensor probe to within a pre-determined distance of the housing against the bias; and
   producing an alarm signal in response to the measured localized capacitance.

5. The process of claim 4, wherein the pushing step changes the localized capacitance between the sensor probe and the housing such that it approaches the localized capacitance when the sensor probe is biased a set distance away from the housing and an amount of the contaminating fluid in the base fluid is above the pre-set threshold.

6. The process of claim 1, wherein the contaminant detector is mounted vertically in a bottom wall of the tank.

7. The process of claim 1, wherein the contaminant detector is mounted horizontally in a side wall of the tank.

8. The process of claim 1, wherein the base fluid comprises a fuel and the contaminating fluid comprises water.

9. The process of claim 1, wherein the circuit board is disposed within the core.

10. The process of claim 1, wherein the electrical power is provided from a source external to the tank.

11. A process for detecting the presence of water in a base fluid of fuel, comprising the steps of:
    positioning a contaminant detector having a conductive core, a conductive housing in which the core is slidingly disposed in conductive relation, a sensor probe extending from the core in non-conductive relation, and a circuit board electrically coupled to the sensor probe, in a tank containing the fuel;
    applying electrical power to the circuit board;
    creating an electrical charge in the sensor probe and an opposite electrical charge in the housing to create a closed field loop through the fuel;
    measuring localized capacitance of the fuel in proximity to the sensor probe and the housing; and
    producing an alarm signal in response to a change in the measured localized capacitance to indicate the presence of the water in the fuel above a pre-set threshold.

12. The process of claim 11, wherein the contaminant detector is mounted vertically in a bottom wall of the tank.

13. The process of claim 11, wherein the contaminant detector is mounted horizontally in a side wall of the tank.

14. The process of claim 11, wherein the circuit board is disposed within the core.

15. The process of claim 11, wherein the electrical power is provided from a source external to the tank.

16. The process of claim 11, further comprising the steps of:
biasing the sensor probe a set distance away from the housing;
pushing the sensor probe to within a pre-determined distance of the housing against the bias; and
producing an alarm signal in response to the measured localized capacitance.

17. The process of claim 16, wherein the pushing step changes the localized capacitance between the sensor probe and the housing such that it approaches the localized capacitance when the sensor probe is biased a set distance away from the housing and an amount of water in the fuel is above the pre-set threshold.

18. A contaminant detector disposed within a base fluid for detecting the presence of a contaminating fluid, comprising:
a conductive housing;
a conductive core slidingly disposed within the housing in conductive relation;
a conductive sensor probe extending from the core in non-conductive relation;
means for charging the sensor probe and providing an opposite electrical charge to the core and housing to create a closed field loop through the base fluid;
means for measuring localized capacitance of the base fluid in proximity to the sensor probe and the housing; and
means for producing an alarm signal in response to a change in the measured localized capacitance to indicate the presence of the contaminating fluid in the base fluid above a pre-set threshold.

19. The contaminant detector of claim 18, wherein the housing extends from the proximate end of the core to beyond the distal end of the core, the housing configured such that the sensor probe extends beyond the distal end of the housing in non-conductive relation.

20. The contaminant detector of claim 18, further comprising a sliding seal between the core and the housing adjacent the proximate end of the core.

21. The contaminant detector of claim 18, further comprising a sensor cap mounted over that portion of the sensor probe that extends beyond the housing and a spring biasing the sensor probe away from the housing.

22. The contaminant detector of claim 21, further comprising an insulating washer between the sensor cap and the housing.

23. The contaminant detector of claim 18, further comprising at least two openings in the housing, adjacent the sensor probe.

24. The contaminant detector of claim 18, further comprising an insulator seal cartridge between the core and the sensor probe.

25. The contaminant detector of claim 18, further comprising an insulator between the core and the sensor probe.

26. The contaminant detector of claim 18, wherein the base fluid comprises a fuel and the contaminating fluid comprises water.

* * * * *